(12) United States Patent
Miao et al.

(10) Patent No.: US 11,253,407 B2
(45) Date of Patent: Feb. 22, 2022

(54) ABSORBENT CORE LAYER AND ABSORBENT PERSONAL CARE ARTICLE CONTAINING SUCH LAYER

(71) Applicant: Kimberly-Clark (CHINA) CO., LTD., Shanghai (CN)

(72) Inventors: Lin Miao, Beijing (CN); Han Chen, Beijing (CN); Chun Lei Pu, Beijing (CN)

( * ) Notice: Subject to any disclaimer, the term of this patent is extended or adjusted under 35 U.S.C. 154(b) by 673 days.

(21) Appl. No.: 15/771,131

(22) PCT Filed: Nov. 30, 2015

(86) PCT No.: PCT/CN2015/095908
§ 371 (c)(1),
(2) Date: May 11, 2018

(87) PCT Pub. No.: WO2017/091924
PCT Pub. Date: Jun. 8, 2017

(65) Prior Publication Data
US 2018/0256415 A1  Sep. 13, 2018

(51) Int. Cl.
| A61F 13/533 | (2006.01) |
| A61F 13/512 | (2006.01) |
| A61F 13/47  | (2006.01) |
| A61F 13/537 | (2006.01) |

(52) U.S. Cl.
CPC .......... *A61F 13/533* (2013.01); *A61F 13/512* (2013.01); *A61F 13/4704* (2013.01); *A61F 13/537* (2013.01)

(58) Field of Classification Search
CPC .... A61F 13/472; A61F 13/53; A61F 13/4704; A61F 13/512; A61F 13/533; A61F 13/537; A61F 2013/53044; A61F 2013/530875; A61F 13/534; A61F 2013/15382; A61F 13/53436; A61F 13/5376; A61F 2013/53765; A61F 2013/53782
See application file for complete search history.

(56) References Cited

U.S. PATENT DOCUMENTS

| 2,747,575 A |   | 5/1956 | Mercer |
| 3,749,627 A | * | 7/1973 | Jones, Sr. ............. A61F 13/532 |
| | | | 156/268 |
| 3,766,922 A |   | 10/1973 | Krusko |
| 3,897,784 A |   | 8/1975 | Fitzgerald |

(Continued)

FOREIGN PATENT DOCUMENTS

| CA | 2630713 | 11/2008 |
| CN | 1711062 A | 12/2005 |

(Continued)

*Primary Examiner* — Michele M Kidwell

(57) ABSTRACT

An absorbent core layer (18) for absorbing and retaining body exudate includes a first longitudinally directed end region (25), a second opposing longitudinally directed end region (26), and a middle region (22) positioned between the end regions. The middle region (22) includes a first embossing pattern and has a first thickness. The first longitudinally directed end region (25) and second opposing longitudinally directed end region (26) each include a second embossing pattern different from the first embossing pattern, and also having apertures. The end regions (25, 26) each have a second thickness, the second thickness being less than the first thickness.

18 Claims, 7 Drawing Sheets

(56) References Cited

U.S. PATENT DOCUMENTS

| | | | |
|---|---|---|---|
| RE29,789 E | 10/1978 | Kolbach | |
| 4,414,255 A | 11/1983 | Tokuyama | |
| 4,435,178 A | 3/1984 | Fitzgerald | |
| 4,449,979 A | 5/1984 | Holtman | |
| 4,596,567 A * | 6/1986 | Iskra | A61F 13/53756 604/368 |
| 4,639,254 A | 1/1987 | LeGault | |
| 4,685,915 A | 8/1987 | Hasse | |
| 4,762,521 A * | 8/1988 | Roessler | A61L 15/60 604/385.26 |
| 5,514,104 A | 5/1996 | Cole | |
| 5,562,649 A * | 10/1996 | Chauvette | A61L 15/48 604/375 |
| 5,788,684 A * | 8/1998 | Abuto | A61F 13/532 604/368 |
| 5,833,679 A | 11/1998 | Wada | |
| 5,941,863 A * | 8/1999 | Guidotti | A61F 13/535 604/378 |
| 6,171,291 B1 | 1/2001 | Osborn, III | |
| 6,441,268 B1 | 8/2002 | Edwardsson | |
| 6,958,430 B1 | 10/2005 | Marinelli | |
| 6,986,761 B1 * | 1/2006 | Hines | A61F 13/4704 604/385.01 |
| 7,145,054 B2 | 12/2006 | Zander | |
| 7,727,212 B2 | 6/2010 | Sakai | |
| 7,959,622 B2 | 6/2011 | Kudo | |
| 8,211,078 B2 * | 7/2012 | Noel | A61F 13/15203 604/385.31 |
| 8,398,915 B2 | 3/2013 | Alkmin | |
| 8,847,002 B2 | 9/2014 | Goh | |
| 9,579,238 B2 * | 2/2017 | Noel | A61F 13/474 |
| 10,052,242 B2 * | 8/2018 | Bianchi | A61F 13/539 |
| 2004/0243084 A1 * | 12/2004 | Yoshimasa | A61F 13/15203 604/385.01 |
| 2005/0124953 A1 * | 6/2005 | Woltman | A61F 13/4704 604/385.01 |
| 2007/0100307 A1 * | 5/2007 | Nomoto | A61F 13/4704 604/378 |
| 2007/0135787 A1 * | 6/2007 | Raidel | A61F 13/15723 604/383 |
| 2008/0004581 A1 * | 1/2008 | Babusik | A61F 13/53747 604/380 |
| 2008/0281287 A1 * | 11/2008 | Marcelo | A61F 13/4756 604/383 |
| 2011/0092944 A1 * | 4/2011 | Sagisaka | A61F 13/15203 604/385.101 |
| 2012/0004633 A1 * | 1/2012 | R. Marcelo | A61F 13/4758 604/378 |
| 2012/0078209 A1 * | 3/2012 | Sakai | A61F 13/4756 604/378 |
| 2012/0265162 A1 * | 10/2012 | Kuramochi | A61F 13/4758 604/385.101 |
| 2013/0289510 A1 * | 10/2013 | Nakajima | A61F 13/49426 604/378 |
| 2014/0005623 A1 * | 1/2014 | Wirtz | A61F 13/539 604/366 |
| 2015/0005729 A1 * | 1/2015 | Nakao | A61F 13/15658 604/374 |
| 2015/0173977 A1 * | 6/2015 | Stelzig | A61F 13/53 604/378 |
| 2015/0174280 A1 * | 6/2015 | Stelzig | A61L 15/58 604/366 |
| 2015/0257943 A1 * | 9/2015 | Noel | A61F 13/472 604/369 |

FOREIGN PATENT DOCUMENTS

| | | |
|---|---|---|
| CN | 101347370 A | 1/2009 |
| CN | 101815487 A | 8/2010 |
| CN | 101874756 A | 11/2010 |
| CN | 102949268 A | 3/2013 |
| CN | 202821854 U | 3/2013 |
| CN | 103140196 A | 6/2013 |
| CN | 202960954 U | 6/2013 |
| CN | 104546307 A | 4/2015 |
| EP | 0249405 B1 | 8/1992 |
| GB | 2089214 A1 | 6/1982 |
| JP | 5232553 B2 | 7/2013 |
| WO | 03105738 A1 | 12/2003 |
| WO | 13150921 A1 | 10/2013 |

* cited by examiner

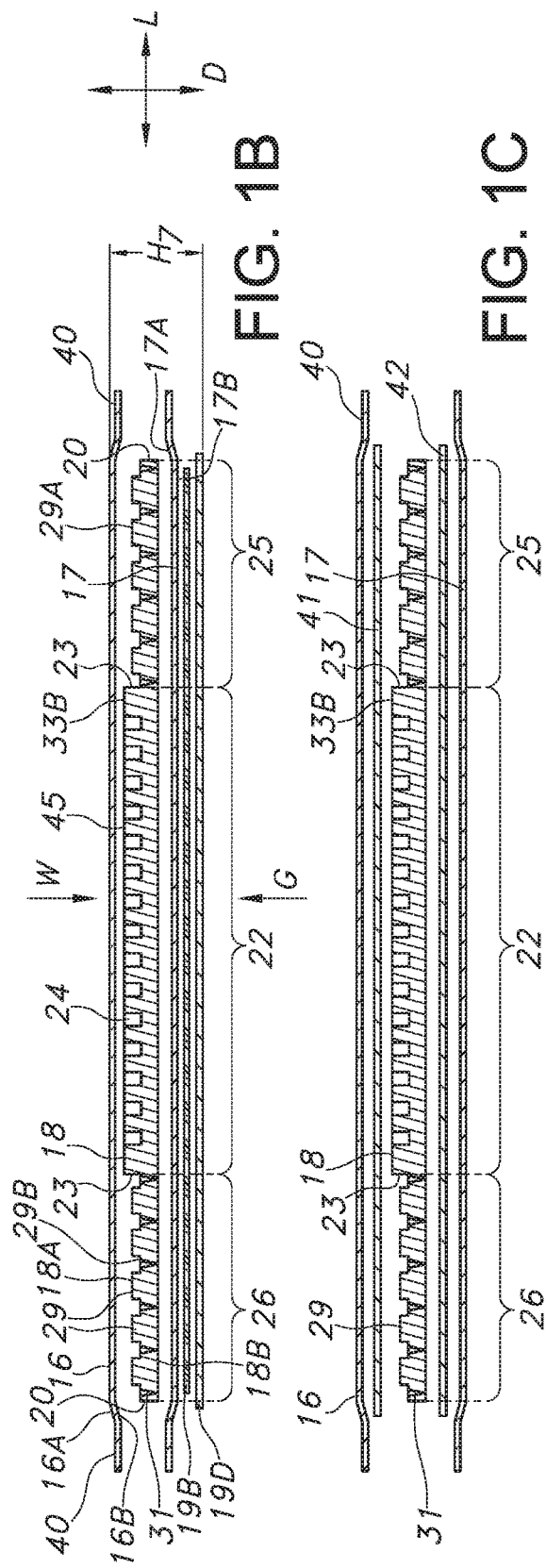
FIG. 1B
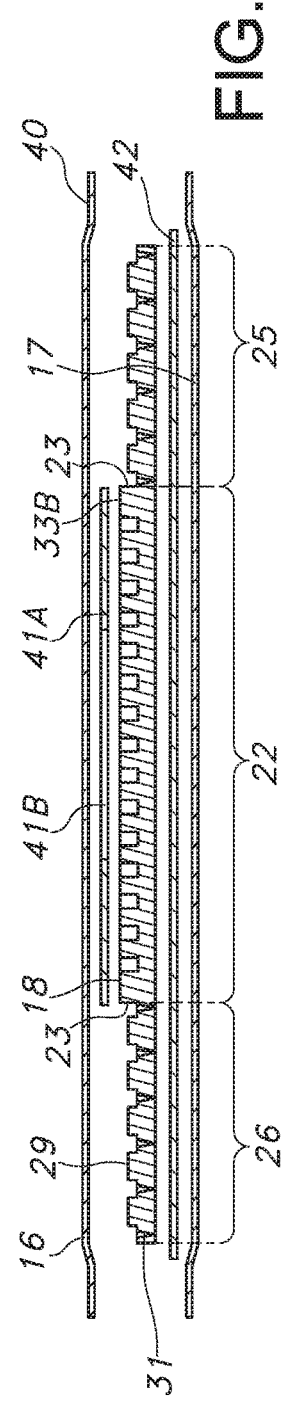
FIG. 1C
FIG. 1D
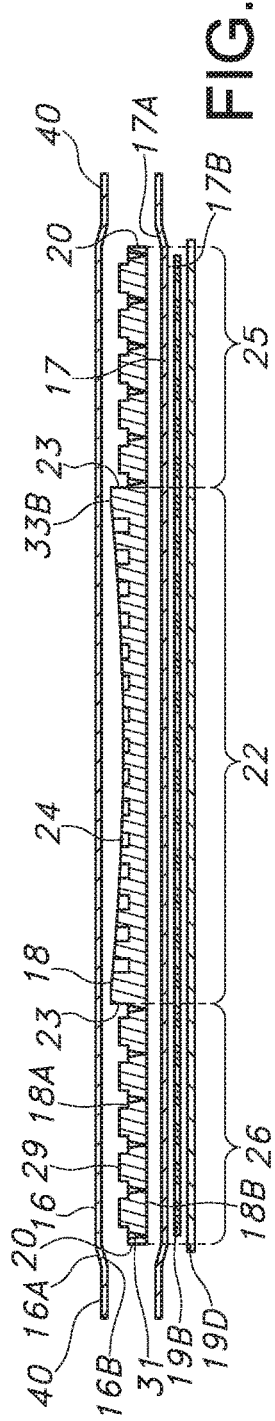
FIG. 1E

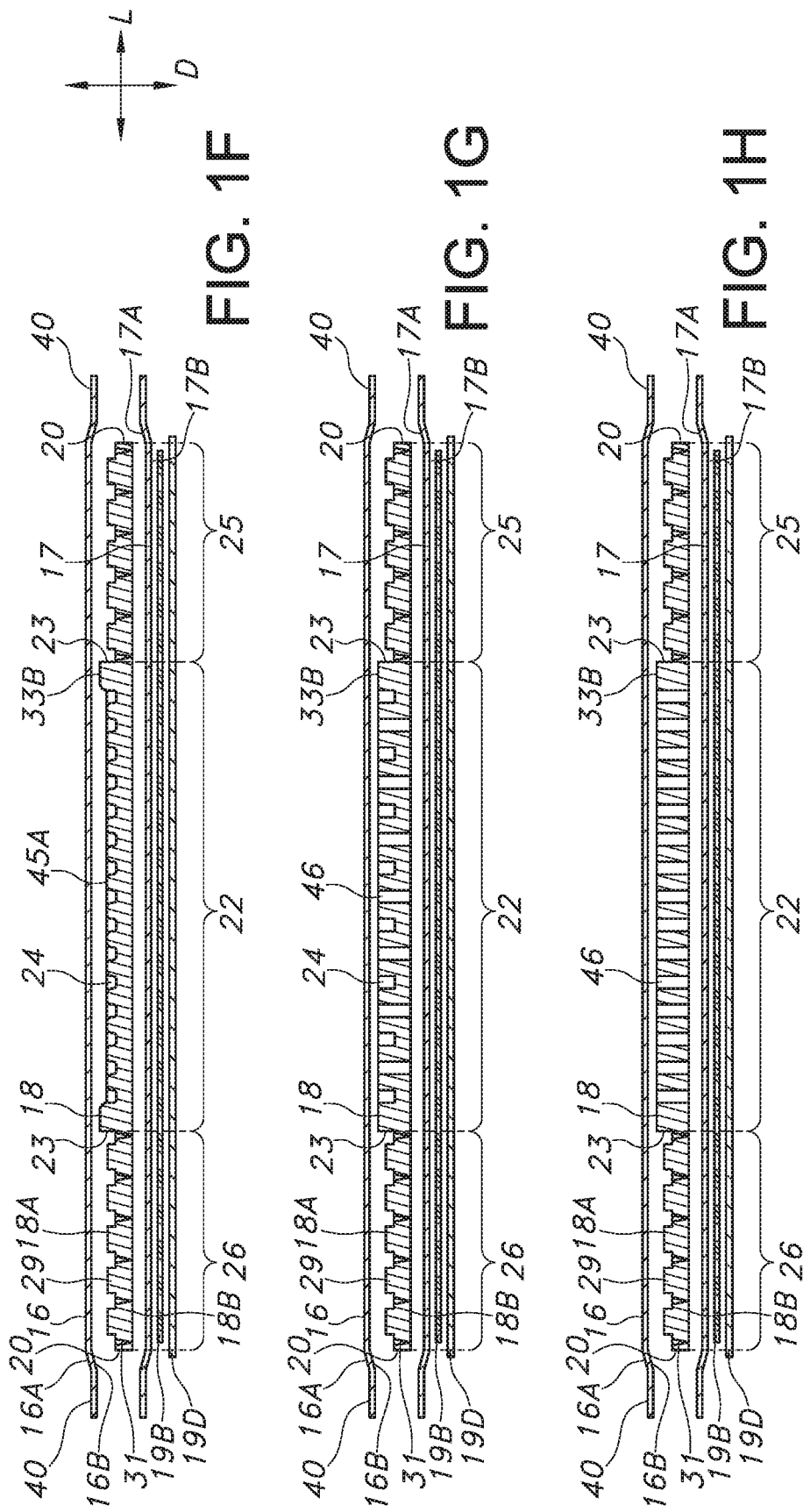

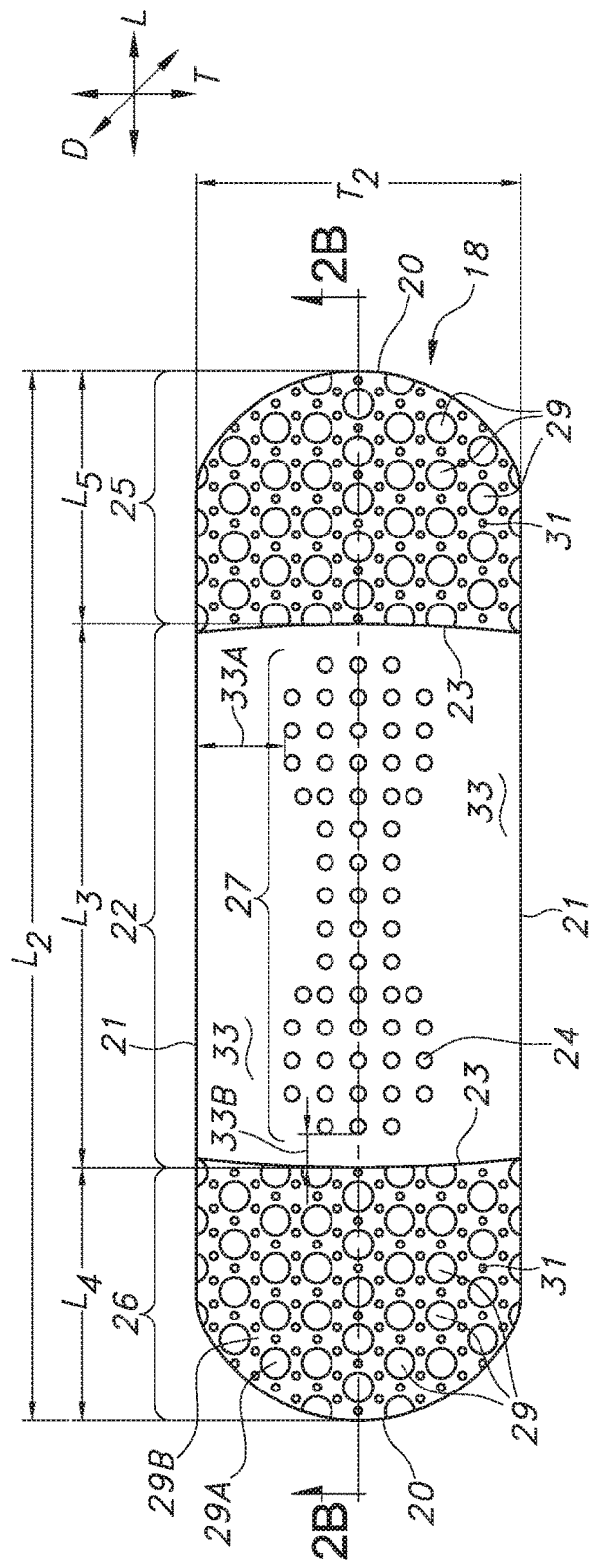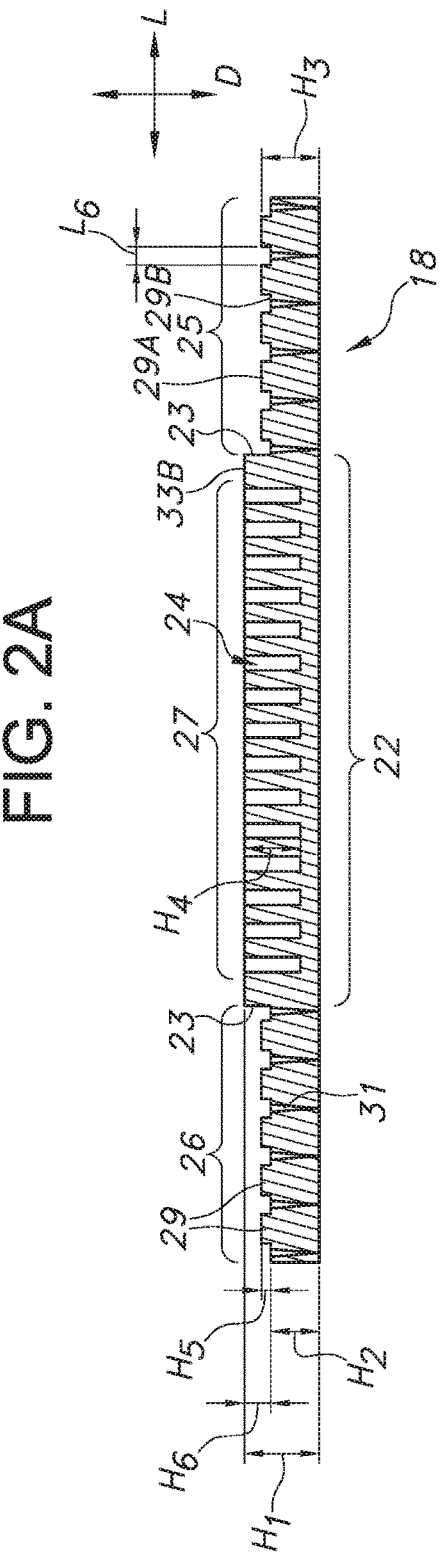
FIG. 2A
FIG. 2B

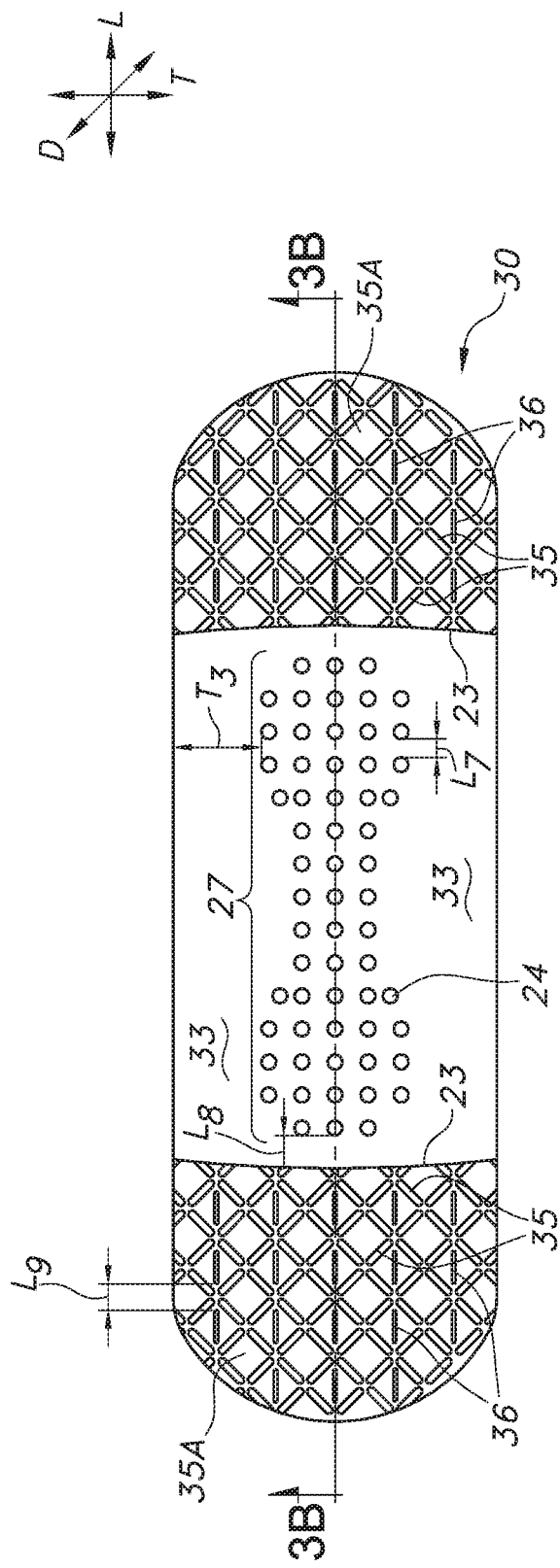
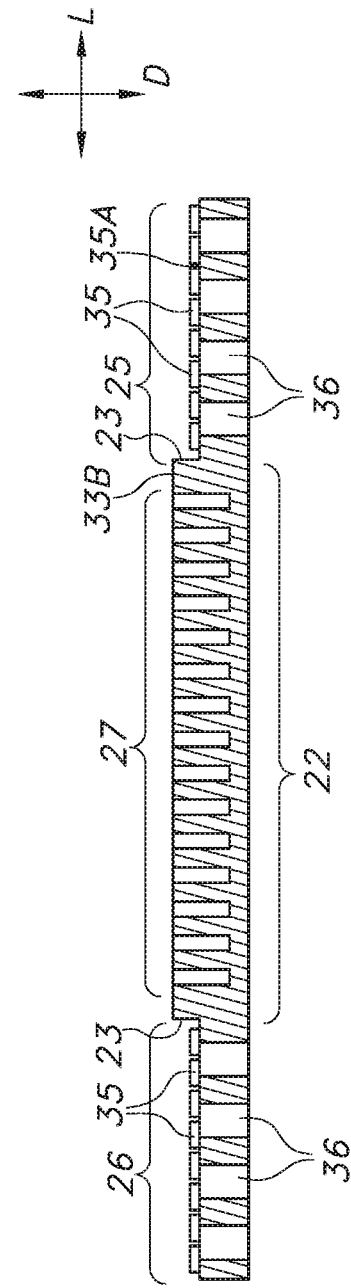
FIG. 3A
FIG. 3B

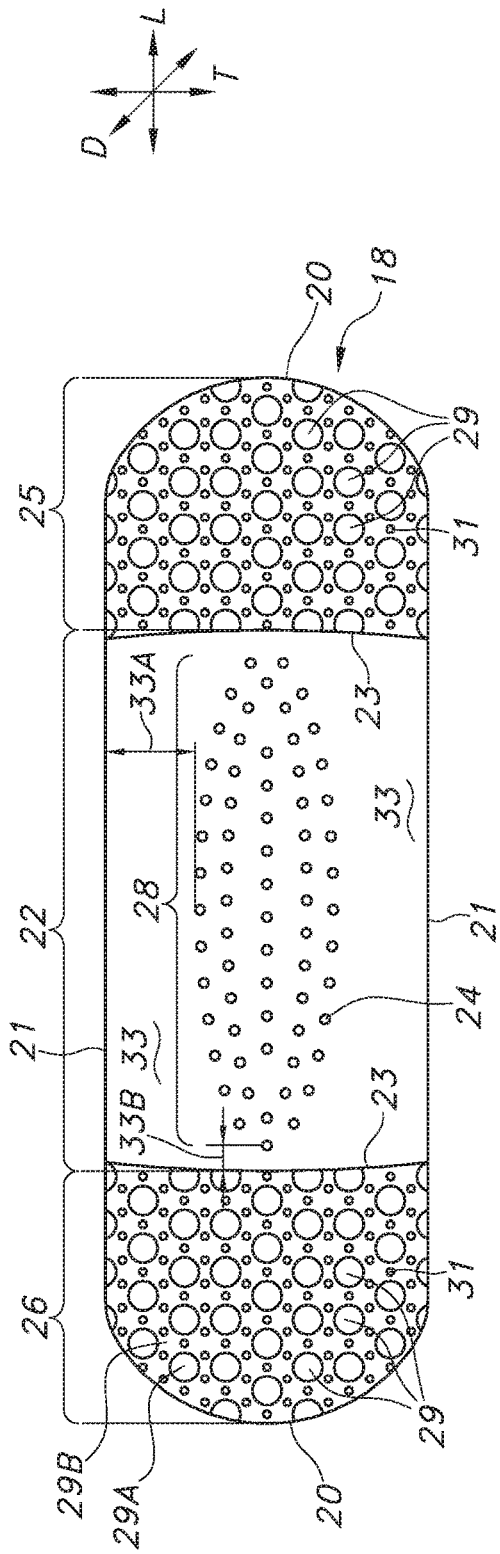
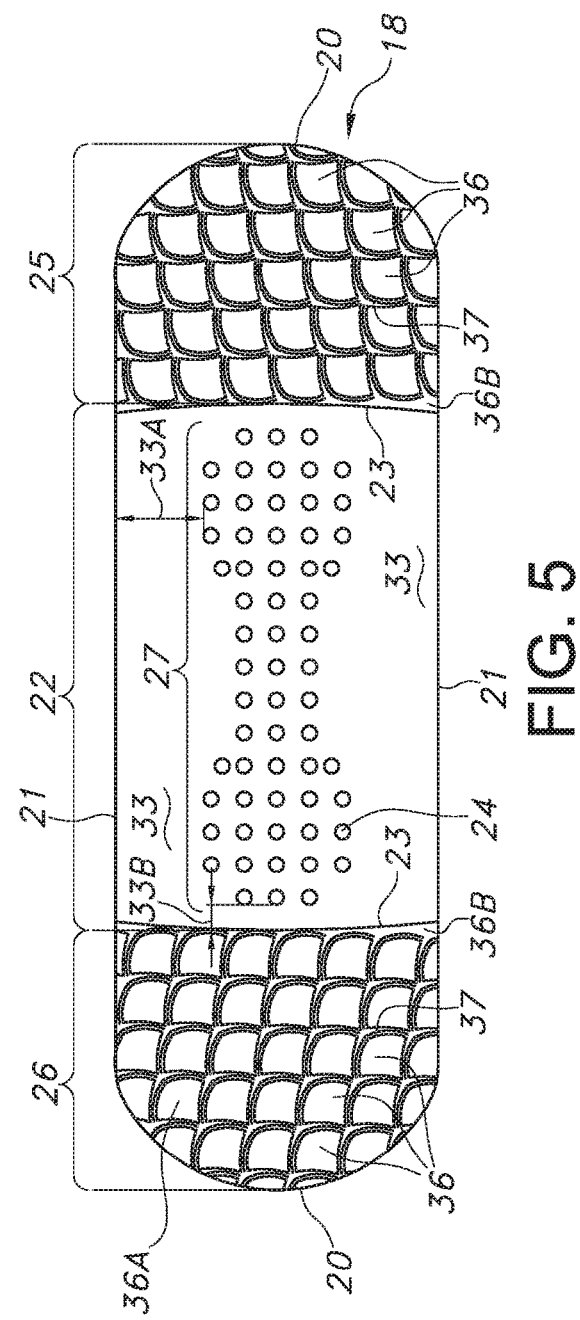

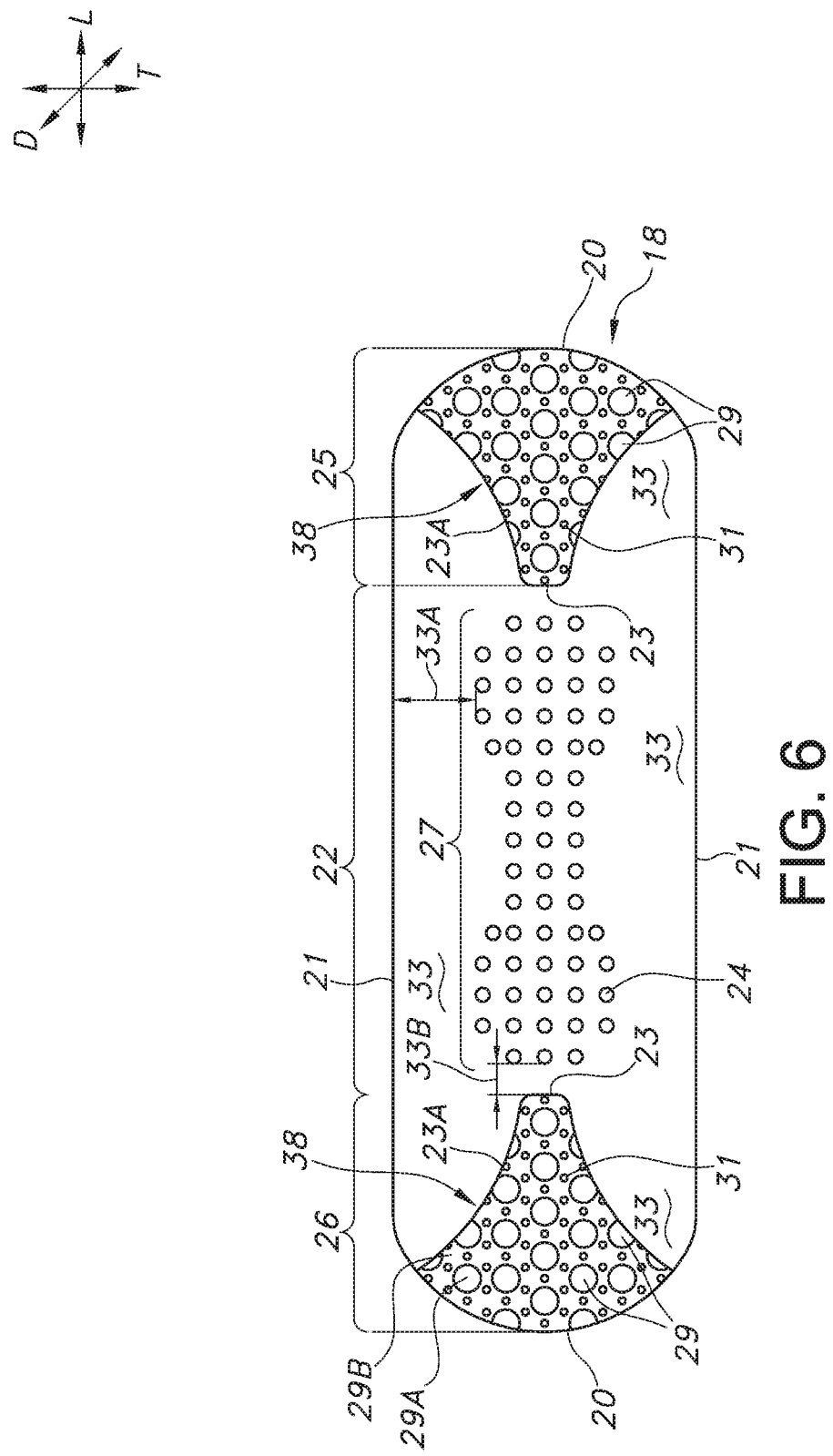

ABSORBENT CORE LAYER AND ABSORBENT PERSONAL CARE ARTICLE CONTAINING SUCH LAYER

FIELD OF THE INVENTION

The present invention is generally directed to absorbent core layers for use in personal care absorbent articles and the absorbent articles containing such core layers. In particular, the present invention is directed to absorbent core layers which are both embossed and apertured, for use in personal care absorbent articles.

BACKGROUND OF THE INVENTION

Feminine and adult hygiene, absorbent personal care articles are often used to protect consumer undergarments and outer garments from soiling, and to collect and retain body exudates such as menses, blood, or urine. These product categories include articles such as panty liners, sanitary napkins, pads, and disposable panties, incontinence inserts and pant-like absorbent garments. Such articles are most commonly placed in the crotch region of an undergarment or outer garment during use. In the context of such articles, absorbency and comfort are two main article attributes and areas of concern for the wearers of such articles. In particular, wearers are often interested in knowing that such articles will sufficiently absorb body exudates in order to protect their undergarments, outer garments, or bed sheets from soiling. Wearers also desire articles which are comfortable to wear, allowing freedom of movement within their garments.

Frequently, such absorbent personal care articles include a liquid permeable topsheet layer (for directly contacting a wearer's body and through which body exudate is passed into the article), a liquid impermeable backsheet layer (for directly contacting and protecting the wearer's undergarments and outer garments from soiling), and a cellulosic or combination, cellulosic and synthetic fibrous/fluff core layer, sandwiched and sealed between the topsheet and backsheet layers (for retaining body exudates that have been absorbed into the article through the topsheet layer). While other functional layers may also be included within absorbent personal care articles, the lofty fluff-core layer is traditionally the primary absorbent layer of articles, and also the thickest layer, and therefore accounts for much of the overall bulkiness of the articles themselves. While such fluff-core layer can enhance the overall softness and cushion-like feel of the absorbent articles, such bulkiness also may have the disadvantage of restricting wearer movements within their undergarments. Such thick layer may also contribute to the ability of passersby to see the profile of the absorbent article through a user's undergarments and/or outer garments. Therefore, despite such fluff layers (in some instances, airlaid materials) providing emotional and physical comfort to wearers of the articles (in terms of confidence of absorbent ability, and cushiony feel), and significant actual absorbent capacity, the large bulk of the core layers has often detracted from the overall benefits of such articles, and in some instances, deterred would-be consumers from regularly using such articles, who could otherwise derive benefit from them. Furthermore, the packaging options available to manufacturers of the more bulky absorbent articles are limited. Such bulky articles may not be easily folded for compact storage, and therefore the embarrassing identification of such packaged articles by passersby may be relatively easy. Wearers are therefore interested in having such articles demonstrate a relative thinness so as to reduce the bulky feeling created by thick internal layers, while still providing sufficient absorbency. Wearers also desire to increase the overall inconspicuousness of such articles, especially when viewed through a wearers' garments by passersby.

In order to address these consumer and manufacturing concerns, absorbent article manufacturers have sought to reduce the thickness of the cellulosic fluff-core layer or combination, cellulosic and synthetic fibrous fluff-core layer typically found in absorbent articles. Alternative core layer structures have therefore been pursued that include less bulk. For instance, core layers have been designed with less fluff, and which also include superabsorbent polymer (i.e. SAP particles) components. While such SAP materials have allowed for the design of thinner layers, SAP material adds significant expense and manufacturing complexity to an absorbent article. Such SAP may also create stiffness in the absorbent core layer, if present in large percentages or in specific zones across such core layers. There is therefore still a need for reduced-bulk absorbent core layers and absorbent articles containing them, which have either none or relatively little SAP content, without compromising absorbency.

Another alternative to a reduced-bulk fluff layer with SAP, has been a core layer which has either been compressed along its entire length and width dimensions, or only along part of its dimensions, so as to create a generally thinner structure prior to laminating it to other layers within the absorbent article. In order to enhance the thinness, absorption speed, and overall effectiveness of absorbent core layers within absorbent personal care articles, it has also been common for the compressed absorbent core layers to include various shaped-embossment features in the layer (rather than having a mere smooth, compacted appearance). These embossments or discrete areas of compression, have been in the forms of channels or repeat patterns, such as separated circular patterns. Such embossments are illustrated for example, in U.S. Pat. No. 4,414,255 to Tokuyama et al., and United States Patent Publication 2008/0004581A1 to Babusik et al. Such embossments typically traverse across the entire width and length of the embossed core layer(s). Alternatively, as seen in JP 4628603 to Masaki et al., the embossments may be absent from a central region of the absorbent core layer, such that a raised and cushion-like central exudate-deposition zone (which is to be placed under or adjacent a user's genitalia) is surrounded by more flattened, embossed regions. While such embossments effectively reduce fluff core layer bulk, provide for enhanced leakage control, and can enhance the spread of the body exudate to peripheral areas of the absorbent core layer, the compressed or embossed areas of such absorbent core layers tend to be stiff (as a result of the compressed cellulosic or synthetic fibers forming higher density areas). The embossed areas therefore resist bending in these regions as a wearer moves about. As a result, such embossments frequently reduce a wearer's comfort at least in these article areas, as the wearer is constantly aware of the presence of a rigid structure in their undergarment. While bend resistance may be advantageous in certain situations, and for certain areas of a product so as to avoid issues with bunching of the product in a wearer's undergarment, such bend resistance should be targeted and not reduce the wearer's perception of softness of the article. There is therefore a need for absorbent core layers which benefit from the fluid distribution properties of embossments (densified regions), but which also retain a certain ability to flex, bend and demonstrate softness, in or adjacent the embossed areas, as a wearer moves about.

While references such as Babusik et al. and International Patent Publication WO2006/105305 to Buiatti et al., also illustrate the use of differently shaped embossments in various regions of an absorbent article, each of such embossments still create a certain stiffness that impacts a wearer's comfort. There is therefore a need for an absorbent core layer and absorbent article which takes functional advantage of different embossments in various regions, while still allowing for flexibility of the layer.

So as to either create bend lines in an absorbent article, or to increase the speed at which absorbent core layers take in body exudate, it is not uncommon for such layers to include targeted cuts or apertures that direct body exudate either completely through an absorbent core layer to subjacent layers, or alternatively, to lower levels within the same absorbent core layer. For instance, cuts and apertures are described in U.S. Pat. No. 7,959,622 to Kudo et al. at specific pad side areas, to provide a targeted hinge. Such apertured or cut core layers do not however, also assist in providing for targeted thinness of a single layer while accelerating exudate capture in the thinner pad areas. In contrast, such cuts or apertures allow for the hinging of a relatively thick layer adjacent the longitudinal side edges of a pad. Therefore, despite the use of apertures in core layers, a need still exists for absorbent core layers which provide for both reduced bulk and flexibility in most core layer regions, and which also provide for accelerated or targeted exudate capture in other regions of the same core layer. Such unitary core layer construction which would address both needs, could reduce manufacturing complexity and lower raw material costs, especially if the need for higher SAP content is reduced.

While absorbent articles often include raised central areas in order to provide a more cushion-like feel at the article "insult" area that is to be placed directly under that portion of the wearer's anatomy from which body exudate is released (while also maintaining close association of the article with likely exudate deposition, anatomical areas), such comfort does not often extend to the outermost regions of the articles. Such outermost regions are frequently less comfortable as a result of stiffened, embossed areas. There is therefore a need for a pad with thinner regions, that do not sacrifice comfort as a result of having such thinner regions. There is a further need for a unitary absorbent core layer which provides these advantages without necessarily relying on complex manufacturing processes, costly raw materials, or multiple stacked core layers for their benefits.

SUMMARY OF THE INVENTION

An absorbent core layer for absorbing and retaining body exudate includes a longitudinal, transverse, and depth direction. The layer also includes a first end region, a second opposing end region, and a middle region positioned between the first and second opposing end regions. The middle region is for placement under the source of body exudate. The middle region includes either a first embossing pattern having individual embossment features, or a pattern of apertures. The middle region also has a first maximum thickness. The first end region and the second opposing end region each include a second embossing pattern having individual embossment features, different from those of the first embossing pattern if present, and also having apertures between the second embossing pattern individual embossment features. The apertures may also surround the individual embossment features of the second embossing pattern. The first end region and the second opposing end region each have a second maximum thickness. In one embodiment, the second maximum thickness is less than the first maximum thickness. Such end regions may be visually distinguished from the middle region by either the thickness differences, the embossing pattern differences, or a combination of both the thickness differences and embossing pattern differences.

In one alternative embodiment the middle region includes a central area. The middle region includes a first embossing pattern and the first embossing pattern in the middle region is present in the central area. In an alternative embodiment, the first embossing pattern is comprised of individual embossment features each in the shape of a circle. In still another alternative embodiment, the absorbent core layer is of a single layer construction. Alternatively, the absorbent core layer is formed of multiple layers. In yet another alternative embodiment, the regions are distinguished from one another along parallel lines or substantially parallel lines. In still another alternative embodiment, an absorbent article has a topsheet layer, a backsheet layer and an absorbent core layer sandwiched and sealed between the topsheet and backsheet layers. The absorbent core layer of the absorbent article is the inventive absorbent core layer.

In still another alternative embodiment, the end regions extend outward from the middle region along the longitudinal direction of the absorbent core layer. In another alternative embodiment, the second maximum thickness is less than the first maximum thickness. In another alternative embodiment, the middle region includes apertures. In still another alternative embodiment, the middle region includes both apertures and a first embossing pattern of individual embossment features.

In another alternative embodiment, an absorbent core layer for absorbing body exudate, has a longitudinal, transverse, and depth direction. The absorbent core layer includes a first longitudinal end region, a second opposing longitudinal end region, and a middle region positioned between the first longitudinal end region and the second opposing longitudinal end region. The middle region is for placement under the source of body exudate. The middle region includes a first embossing pattern of individual embossment features, and has a first thickness. The first longitudinal end region and the second opposing longitudinal end region include a second embossing pattern of individual embossment features different from the first embossing pattern individual embossment features, and has apertures between the second embossing pattern individual embossment features. The first and second opposing longitudinal end regions have a thickness less than that of the middle region. The apertures of the end regions are selected from the group consisting of dot-like apertures and slits.

In yet another alternative embodiment, the first and second opposing longitudinal end regions have a thickness of between about 0.75 mm and 5.0 mm, in one alternative embodiment, between about 0.75 mm and 3.0 mm, in one alternative embodiment, between about 0.8 mm and 1.5 mm. In still another alternative embodiment, the embossing pattern of the first and second opposing longitudinal end regions are configured in the shapes of either circles, squares, ovals, diamonds, lines, dots, sectors, or waves, and the apertures are in the shapes of either circles, lines, or dashes. In still another alternative embodiment, the second embossing pattern of the first and second opposing longitudinal end regions covers between about 10 and 100 percent of the surface area of each end region. In another alternative embodiment, the apertures of the end regions are aligned along either the longitudinal or transverse direction, alternatively along the longitudinal direction of the absorbent core layer. In yet another alternative embodiment, the apertures of the end regions are oriented along the longitudinal direction of the absorbent core layer. In still another alternative embodiment, the apertures are present at each of the end regions so as to cover between about 2 and 20 percent of each end region total surface area. In another alternative embodiment, the first embossing pattern of the middle region covers between about 0.5 and 10 percent of the middle region surface area. In another alternative embodiment, the absorbent core layer has an overall length of between about 135 mm and 400 mm and the middle region has a length of between 20 and 80 percent of the overall absorbent core layer length. In still another alternative embodiment, one of the end regions may be between about 10 and 60 percent, alternatively between about 10 and 50 percent of the overall length of the absorbent core layer.

BRIEF DESCRIPTION OF THE DRAWINGS

A full and enabling disclosure of the present invention is set forth more particularly in the remainder of the specification, including reference to the accompanying figures, in which:

FIG. 1B illustrates a longitudinally directed cross-sectional view of the absorbent article of FIG. 1A taken along lines 1B-1B.

FIG. 1C illustrates a longitudinally directed cross-sectional view of an alternative embodiment of the absorbent article of FIG. 1A, taken at approximately the same location as lines 1B-1B.

FIG. 1D illustrates a longitudinally directed cross-sectional view of an alternative embodiment of the absorbent article of FIG. 1A, taken at approximately the same location as lines 1B-1B.

FIG. 1E illustrates a longitudinally directed cross-sectional view of an alternative embodiment of the absorbent article of FIG. 1A, taken at approximately the same location as lines 1B-1B.

FIG. 1F illustrates a longitudinally directed cross-sectional view of an alternative embodiment of the absorbent article of FIG. 1A, taken at approximately the same location as lines 1B-1B.

FIG. 1G illustrates a longitudinally directed cross-sectional view of an alternative embodiment of the absorbent article of FIG. 1A, taken at approximately the same location as lines 1B-1B.

FIG. 1H illustrates a longitudinally directed cross-sectional view of an alternative embodiment of the absorbent article of FIG. 1A, taken at approximately the same location as lines 1B-1B.

FIG. 2A illustrates a top plan view of an absorbent core layer itself, in accordance with the invention.

FIG. 2B illustrates a longitudinally directed cross-sectional view of the absorbent core layer of FIG. 2A taken along lines 2B-2B.

FIG. 3A illustrates a top plan view of an alternative embodiment of an absorbent core layer in accordance with the invention.

FIG. 3B illustrates a longitudinally directed cross-sectional view of the absorbent core layer of FIG. 3A taken along lines 3B-3B.

FIG. 4 illustrates a top plan view of an alternative embodiment of an absorbent core layer in accordance with the invention.

FIG. 5 illustrates a top plan view of an alternative embodiment of an absorbent core layer in accordance with the invention.

FIG. 6 illustrates a top plan view of an alternative embodiment of an absorbent core layer in accordance with the invention.

DEFINITIONS

Figure 1A:
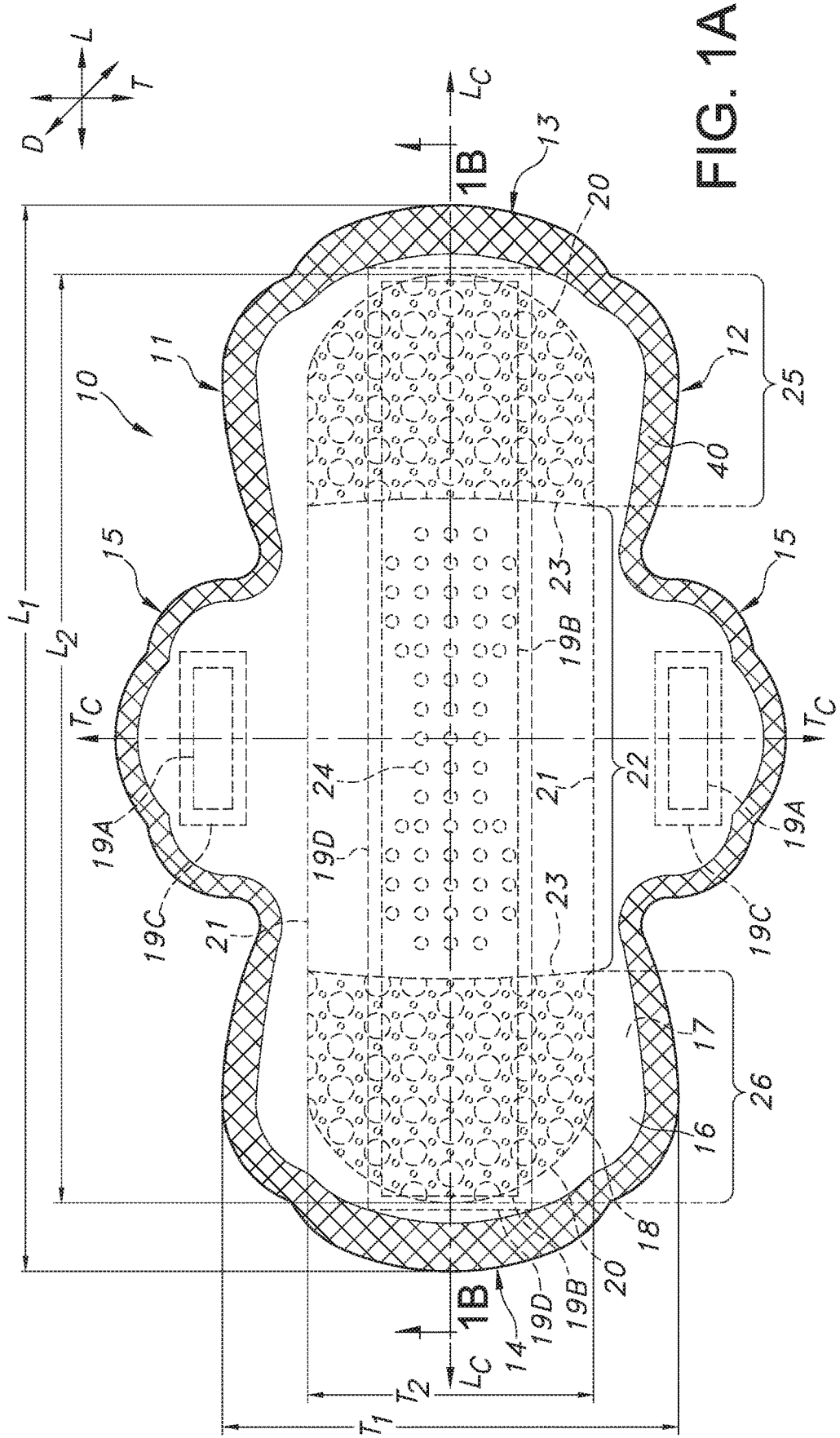
FIG. 1A illustrates a top plan view of an absorbent article with absorbent core layer shown in phantom lines, in accordance with the invention.

As used herein, the terms "nonwoven" and "nonwoven fabric or web" refer to a web having a structure of individual fibers or threads which are interlaid, but not in an identifiable manner as in a knitted fabric. Nonwoven fabrics or webs have been formed from many processes such as for example, meltblowing processes, spunbonding processes, coform processes in which fluff material is formed with an extruded polymeric material, such as a meltblown material, airlaying, hydroentangling, and bonded carded web processes (such as through-air bonded carded webs or TABCW).

As used herein, the terms "embossment," "embossed feature", and "embossment feature", are used interchangeably and refer to a structural feature formed when a layer of material is compressed or depressed at a discrete location (in accordance with known embossment techniques) such that the embossed layer still includes some material from the embossed layer, located directly beneath the area of embossment. Essentially, areas of the embossed layer which are embossed (the embossments), are compressed so as to increase layer density, but are not perforated. The embossment features do not pierce through the entire thickness of the embossed layer. Multiple embossment features shall make up an "embossing or embossed pattern." An embossing or embossed pattern (such as 27) shall either include a series of depressions (such as 24, also known as negative embossments for the purpose of this disclosure), a pattern of protuberances (such as 29, also known as positive embossments for the purpose of this disclosure), or a combination of each. Negative embossments may be considered the more traditional embossments in which only recesses are formed in a layer, for example when viewed from a wearer-facing surface of an article. Such recesses may extend downward along an article depth direction, from a wearer-facing surface of an article layer to a garment-facing surface of an article layer.

Such negative embossments may be formed for example, by passing a sheet material through a nip of a first patterned roll (which has protruding structures along its surface) and a smooth or rubber-covered mated roll, or alternatively against a mated roll having recesses corresponding to the protruding structures of the first patterned roll. Positive embossments may be formed from a pattern roll that includes either recesses, or protrusions and recesses along its surfaces, and that is pressed against a smooth or rubber-covered mated roll. An example of a positive embossing pattern may be seen for example in FIG. 1B at 29, in which individual protruding circles 29A extend from depressed, (and surrounding) trough-like embossment features 29B. In such a situation, both the protrusions and depressed areas are part of a larger embossing pattern.

Embossing may be accomplished through the application of heat, pressure, ultrasonic energy or a combination thereof.

Examples of embossing techniques and patterns may be found for example in U.S. Pat. No. 7,686,790 to Rasmussen et al., U.S. Pat. No. 7,145,054 to Zander et al., and U.S. Pat. No. 4,333,979 to Sciaraffa et al., each of which is hereby incorporated by reference thereto in its entirety, to the extent not inconsistent with this disclosure. In one embodiment, embossments may be created by a pair of closely associated embossing rolls, which embossing rolls include upon one or both of their surfaces a pattern of raised or depressed features, or pins, which raised or depressed features or pins are designed not to penetrate completely through the layer that is to be embossed. In a further embodiment, such embossing rolls may include a nip formed between a patterned and smooth roll. Alternatively, such embossment rolls may be designed to provide both embossment features and aperture features, as described further below. In one embodiment, such embossment features are of a circular or curvilinear shape and each have a diameter of between about 0.5 and 10 mm, alternatively between about 1 and 3 mm. If such individual embossment features are of another shape such as abstract, square, or rectangular, such shape in one embodiment, has a longest dimension across the embossment feature of between about 0.5 and 10 mm, alternatively between about 1 and 3 mm. In a further embodiment, such embossment features occupy a total surface area on an absorbent article of between about 1,000 and 20,000 $mm^2$.

The term embossment is distinguishable for the purposes of this disclosure, from the term "aperture", which term "aperture" is used to define a structure in which a through-channel (that is a continuous perforation) is created between a first outer surface of an apertured layer and a second, opposing outer surface of the apertured layer, such that exudate may flow directly through the channel from the first outer surface of the apertured layer to the opposing second outer surface without passing through a fibrous matrix. An aperture is formed from either a mechanical contact process (such as by a perforating pin) or a fluid forming process. The normally formed interstitial fibrous spaces of a nonwoven web (that has not been exposed to further treatment or processing following web formation) are not considered apertures under this definition. In one embodiment, the area of each of the openings of such apertures is between about 0.12 and 80 $mm^2$, alternatively, between about 0.8 and 12 $mm^2$. In a further embodiment, the diameter of circular aperture openings in accordance with this disclosure is between about 0.5 and 50 mm, alternatively between about 1 and 5 mm. Such apertures may be created by known aperturing techniques, such as for example, by punching, melting, perforating, pin-type hole-forming techniques, and fluid contacting methods. Such aperturing may remove material from the apertured layer, and/or compress material along the walls of the through-channels formed by the aperturing process, but which also places an opening through both opposing outer surfaces of the apertured sheet material (and in some instances, also produces a hanging piece of material off of one outer surface), such that a continuous through-channel extends between the two outer surfaces of the apertured sheet material. Examples of aperturing techniques are further described in international patent publication WO2007/035038A1 to Lyu et al., and U.S. Pat. No. 8,387,497 to Raidel et al., each of which is hereby incorporated by reference thereto in its entirety, to the extent not inconsistent with this disclosure. For the purposes of this disclosure, the term "aperture" shall in one embodiment, also include a discrete linear, dash-like cut or slit feature that extends through the entire thickness of the sheet material. Such slits are described for example in the noted Raidel reference.

For the purposes of this disclosure, the term "height" shall refer to a layer, layer region, or absorbent article size dimension along the depth direction of the respective layer, layer region, or absorbent article. It shall be used interchangeably with the term "thickness". The term "width" shall refer to the layer, layer region, or article size dimension along the transverse direction.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures. While not illustrated in most figures except where additional placement emphasis is desired, it should be understood that traditional article construction, or garment adhesive (or other bonding technology) is to be used to fasten the various layers of the described articles together, or to fasten the articles to a wearer's undergarments. Such construction adhesive or other bonding technology is desirably placed or practiced so as not to interfere with the flow of body exudate through the liquid permeable and absorbent layers of the article. Other contemplated bonding techniques include for example, ultrasonic, pressure, and thermal bonding techniques.

An absorbent core layer and absorbent article containing such layer (each having a longitudinal direction, a central longitudinal direction, a transverse direction, an optional central transverse direction, and a depth direction) are provided in this disclosure, which absorbent core layer includes three distinct regions positioned sequentially along the core layer longitudinal direction. In one embodiment, the absorbent core layer is a unitary structure of homogeneous composition throughout, not itself formed from multiple stacked or separately deposited layers. Such inventive absorbent core layer is in one embodiment, homogeneous in all aspects except as to the physical aspect of density. Alternatively, such absorbent core layer is either a laminate of either previously formed layers, or of a series of sequentially deposited layers (such as airlaid layers), that following lamination or deposition of one layer upon the other, together form a unitary structure. Such unitary structure is "unitary" in that it cannot be physically separated into its original layers if made from multiple layers (the original layers being those present prior to lamination or deposition)

without at least partial destruction or chemical alteration of at least one of the multiple layers. In one embodiment, the unitary structure is a single layer of sheet material, such as for example a fluff-core layer (either entirely made of cellulosic or cellulosic and synthetic fiber fluff, or fluff mixed with SAP). In another embodiment, such absorbent core layer is a laminate of a fluff layer and a separately formed airlaid layer.

The three sequentially positioned regions include a first end region, a middle region adjacent the first end region, and a second end region adjacent to the middle region and opposite from the first end region. In one embodiment, the end regions are not in contact with one another and do not completely surround the middle region, but are each adjacent to it along separated middle region, transverse direction side edges. Therefore in one embodiment, the three regions of the absorbent core layer are visually distinguishable (by different embossment features) from one another when viewed from a top plan view (wearer-facing perspective) at the transverse direction side edges. The middle region, which is desirably also the region of maximum height in the absorbent core layer, includes in one embodiment, a first embossing pattern, positioned within a central area of the middle region and symmetrically about the central longitudinal direction of the absorbent core layer (and article). In one embodiment, the central area is also symmetrically positioned about the central transverse direction of the absorbent core layer (and absorbent article) if such is present. The first embossing pattern is in one embodiment, the deepest embossing pattern in the absorbent core layer, and allows for rapid and direct penetration of body exudate to lower levels of the absorbent core layer. Alternatively, the middle region may include a combination of such embossing pattern, and also apertures. Still further, the middle region may include only apertures in the central area. In one embodiment, the central area of the middle region having the first embossing pattern or apertures, is surrounded by areas of the middle region devoid of embossment features and apertures.

The end regions, each being desirably of lower height (thickness) with respect to the middle region height (thickness), include in one embodiment, a second embossing pattern different from the first embossing pattern. The first embossing pattern includes embossment features which extend relatively deeply into the middle region of the absorbent core layer (and a relatively large percentage of the maximum height of the middle region in which they are located) when compared to the second embossing pattern(s) of the end regions, which include relatively shallower embossment features. The first embossing pattern is in one embodiment, formed to include "negative" embossments such that the embossments created resemble a series of downwardly directed depressions or recesses. The relatively deep depressions of the first embossing pattern allow for the rapid and direct intake of absorbed body exudate to relatively deep levels of the absorbent core layer middle region. The deep embossments (and close proximity to one another) also provide a certain stability to the central area of the middle region.

The two end regions may each include different embossing patterns that differ from one another, and also from the first embossing pattern (not shown). Alternatively, the two end regions may each include the same second embossing pattern that differs only from the first embossing pattern. The second embossing pattern of the end regions, is in one embodiment, formed to include "positive" embossment features (that extend out from the wearer-facing surface of the absorbent core layer), such that it appears to include raised areas contained within the relatively lower maximum height of the end regions. Such positive embossments appear as pillow-like protrusions extending upward from a lower, and surrounding trough-like embossment feature. Essentially, the end regions in one embodiment, include at least two horizontal planes (or levels) in the second embossing pattern when viewed along a longitudinal cross-sectional view. The middle and end region embossing pattern(s) each provide a degree of stability to their respective regions, without the necessity for an additional stabilizing component to be present in the layer.

The end regions also include apertures (such as dot-like holes or slits) in addition to the second embossing pattern, which assist in softening the embossment-induced stiffness of the end regions. Such stiffness may be formed from surrounding trough-like embossment features of the second embossing pattern. The apertures allow for the bending/flexing of the layer at its longitudinal ends, as a wearer moves in his/her undergarments. These apertures are, in one embodiment, formed either between individual embossment features of the second embossing pattern, or alternatively within the trough-like recess if present. Such apertures may also surround individual embossment features of the second embossing pattern. Such apertures are, in one embodiment, oriented along the longitudinal direction of the absorbent core layer. Such apertures may also in one embodiment, be aligned along the longitudinal direction of the absorbent core layer. Such apertures may also provide direct channels for body exudate to flow to layers subjacent the absorbent core layer (such as distribution layers or further absorbent core layers if present). In alternative embodiments, the middle region may include a combination of a first embossing pattern and one or more apertures, or alternatively, a pattern of apertures only. In any event, the middle region first embossing pattern and/or apertures if present, are in one embodiment, situated within the middle region such that they are positioned away from the middle region transverse and longitudinal side edges, so as to create cushion-like structures about the middle region side edges.

In particular, as illustrated in FIG. 1A, which shows a top plan view of an absorbent article 10 containing an absorbent core layer 18 in accordance with the disclosure, the absorbent article 10 (and absorbent core layer 18 shown in phantom lines) has a longitudinal direction L, a transverse direction T, and a depth direction D. The absorbent article 10 and absorbent core layer also include a central longitudinal direction Lc and a central transverse direction Tc. The absorbent article 10 includes an article, wearer-facing surface (designated by "W" in FIG. 1B) and an article, garment-facing surface (designated by "G" in FIG. 1B). The article, wearer-facing surface is the outer surface of the absorbent article 10 that will make direct contact with a wearer while the absorbent article is being used for its intended purpose in a wearer's undergarment. The article, garment-facing surface is the outer surface of the article 10, opposite from the wearer-facing surface that will make direct contact with a wearer's garment or undergarment while the article 10 is being used for its intended purpose. Also, for the purpose of this disclosure, the term "lower" shall refer to a relative position of either a surface or layer within the absorbent article 10 which is beneath the article, wearer-facing surface (along the depth direction). Such a lower surface or layer may be immediately subjacent an upper surface or layer, or several layers beneath it. For example, the backsheet layer 17 (as seen in FIG. 1B) is "lower" within the absorbent article 10 than the absorbent core layer 18 (and subjacent to it).

The absorbent article 10 includes two longitudinally-directed side edges 11, 12 and two longitudinal end edges 13, 14. Along the article longitudinally-directed side edges 11, 12 may optionally be positioned wing projections 15 that extend out from each of the longitudinally-directed side edges 11, 12. The absorbent article 10 includes a liquid permeable topsheet layer 16 (which also forms the article, wearer-facing surface W) a liquid impermeable backsheet layer 17 (which also forms the article, garment-facing surface G), and an absorbent core layer 18, sandwiched and sealed between the topsheet layer 16 and backsheet layer 17. In one embodiment, the topsheet layer 16 is sealed to the backsheet layer 18 along a seal region 40 which is located along the peripheral outer edge of the absorbent article 10. Such seal region 40 may be sealed using any traditional bonding technique, such as for example ultrasonic bonding. In one embodiment, the wing projections 15 are fashioned from portions of the topsheet layer 16 and backsheet layer 17 that extend laterally outward beyond the absorbent core layer 18 longitudinally-directed side edges 21. As can also be seen in FIG. 1A, 1B, the absorbent core layer 18 also includes longitudinal end edges 20, with each of the longitudinal end edges 20 and longitudinally-directed side edges 21 in one embodiment, located inward from the peripheral edges of the absorbent article 10 itself, and also inward from the seal region 40.

Each of the previously described layers within the absorbent article 10 also include a wearer-facing surface and garment-facing surface. For instance, the topsheet layer 16 includes a topsheet layer, wearer-facing surface 16A (also forming the article wearer-facing surface) and a topsheet layer, garment-facing surface 16B. The absorbent core layer 18 includes an absorbent core layer, wearer-facing surface 18A and an absorbent core layer, garment-facing surface 18B. The backsheet layer 17 similarly includes a backsheet layer, wearer-facing surface 17A and a backsheet layer, garment-facing surface 17B (which also forms the article garment-facing surface). Many of these features are visible in the cross-sectional view of FIG. 1B.

The absorbent core layer 18 is shown in phantom lines in FIG. 1A, and is in one embodiment, situated symmetrically about the central longitudinal direction Lc, and also in some instances, the central transverse direction Tc of the absorbent article 10. While the absorbent article 10 of FIG. 1 is shown as being symmetrical, it should be appreciated that asymmetrical shaped articles are also contemplated to be within the scope of the disclosure, such as for example, overnight-style feminine care pads which traditionally include wider back portions (not shown).

On the absorbent article, garment-facing surface (backsheet layer 17 underside) is in one embodiment, situated two wing fasteners 19A (which are desirably adhesive patches placed on the under-surfaces of the wing projections 15), and which are each protected by an adhesive protective release sheet 19C. A centrally-positioned garment adhesive strip 19B is also positioned on the underside of the backsheet layer 17 (garment-facing surface), which too is covered by a protective release sheet 19D. The adhesive patches and strip assist wearers in maintaining the absorbent article 10 in their undergarments while in use. The wing fasteners in particular, assist in maintaining the wings attached to the underside surface of a user's undergarments while the article is in use. It should be appreciated that while adhesive is illustrated, mechanical, hook and loop-type fasteners may be used in addition to, or in place of adhesive patches and strips. Adhesive and protective release sheets are well known in the art, and therefore will not be further described.

In one embodiment, the length L1 of the absorbent article 10 of the disclosure is between about 175 and 600 mm, alternatively, between about 190 and 420 mm. In one embodiment, the width of the absorbent article of the disclosure in the transverse direction T1, is between about 40 and 200 mm, alternatively between about 60 and 170 mm. The width may be uniform along the entire longitudinal direction, or may vary by article design (as shown).

A longitudinal, cross-sectional view of the absorbent article of FIG. 1A, taken along line 1B-1B is shown in FIG. 1B. As seen in the figures, the absorbent core layer 18 includes two absorbent core layer longitudinal ends 20 and two absorbent core layer longitudinally-directed side edges 21. The absorbent core layer 18 is, in one embodiment of a length L2, which is between about 145 and 550 mm, alternatively, between about 160 and 390 mm. In one embodiment the absorbent core layer includes a width T2 in the transverse direction of between about 25 and 180 mm, alternatively, between about 40 and 150 mm. It should be appreciated that while the width T2 (as seen particularly in FIG. 2A) of the absorbent core layer 18 along the transverse direction is substantially uniform except as approaching the longitudinal ends 20 (as seen in FIG. 2A), the width may vary along the longitudinal direction, in alternative embodiments. In one embodiment the ratio of length L1 to length L2 is between about 1.05 to 1 and 1.8 to 1, alternatively, between about 1.1 to 1 and 1.5 to 1.

The absorbent core layer 18 as seen particularly in FIGS. 1A, 2A, 2B includes three distinct regions positioned sequentially along the absorbent core layer longitudinal direction L. The three regions are a middle region 22, flanked by two opposing end regions 25, 26. The middle region 22 is adjacent each end region 25, 26 along a middle region transverse direction side edge/line 23. The middle region transverse direction side edges/lines 23 are, in one embodiment, parallel to each other, or alternatively, substantially parallel (less than or equal to 10 degrees difference with respect to the Tc). In one embodiment, the end regions 25, 26 are not immediately adjacent one another, nor do they surround the middle region 22 on all sides. The middle region 22 is, in one embodiment, situated within the absorbent article such that it is eventually placed by the wearer of the article under that portion of the wearer's anatomy from which body exudate is initially excreted. The middle region 22 is in one embodiment, visually differentiated from the two end regions 25, 26 by at least the embossing patterns and overall height levels of the regions. In one embodiment it is contemplated that the absorbent core layer includes a longitudinal cross-sectional profile have stepped regions, such that the middle region has a distinctly larger height (larger thickness) than the two end regions. In an alternative embodiment, the middle region has a larger height, but the transition in height from the end regions to the middle region is gradual such that the side profile takes on a more curved downward appearance (not shown). In each of these embodiments it is contemplated that the dimensions of the end regions shall be distinguished from the middle region by the location of the end region embossing pattern(s).

In one embodiment, the height or thickness dimensions shall be associated with the maximum height or thickness of the identified layer, layer region, or article. For example, if a height or thickness range is described as being up to 5 mm, it is also contemplated that the identified layer, article, or layer region height may be shorter at other locations along the layer, article, or layer region length, and the height may not be uniform along the longitudinal or transverse directions. For the purposes of this application, an identified layer, article, or layer region may be considered as having a designated maximum height/thickness, if such a height/thickness can be measured at any location within the identified layer, layer region, or article (between the wearer-facing and garment-facing surfaces of the identified layer, layer region, or article respectively).

The middle region 22, includes a first embossing pattern 27 (as seen clearly in FIG. 2A), made up of individual embossment features 24. Such middle region (as seen in FIG. 2A), is of a length L3 along the longitudinal direction L of the absorbent core layer 18 and absorbent article 10. The length L3 is in one embodiment, between about 30 and 300 mm, alternatively, between about 80 and 200 mm, alternatively between about 20 and 80 percent of the overall length L2 of the absorbent core layer 18.

As seen particularly in the longitudinal-sectional view of FIG. 2B, the absorbent core layer 18 includes various heights along its length direction. In particular, the middle region 22 includes a middle region maximum height (or thickness), which is also the largest height of the absorbent core layer 18 when viewed in the cross-sectional view along the layer longitudinal direction. This large height H1 provides a protrusion in the absorbent core layer 18 central area, such that it is closest to the location of a wearer's anatomy from where body exudate is originally excreted. The central area is located symmetrically about the Lc, and also, in one embodiment, about the Tc. In one embodiment, the first embossing pattern 27 is symmetrically positioned about the central longitudinal direction Lc, and is surrounded on all sides by absorbent core layer material 33 devoid of embossment features. The middle region is, in one embodiment, devoid of embossment features 24 along the absorbent core layer, longitudinally-directed side edges 21 by a first amount 33A, and along the transverse direction side edges 23 by a second amount 33B. The larger the amount of middle region devoid of embossment features (along the longitudinally directed side edges 21), the greater the cushiony feel along these longitudinally-directed side edges 21. The first embossing pattern 27 of individual embossment features 24, may be formed in any number of overall pattern shapes, such as oval, dog bone (as shown), rectangular, and abstract. If the first embossing pattern 27 includes portions that are concave with respect to the longitudinal side edge 21, the absorbent core layer provides greater cushion-like feel in use.

The discrete/individual embossment features 24 may have any number of individual shapes, such as for example, circular as shown, other geometric, or abstract shapes, or a combination thereof. In one embodiment, the overall first embossing pattern 27 is located between about 0 and 20 mm from the middle region transverse direction side edges 23, alternatively between about 5 and 10 mm (as demonstrated by L8 on FIG. 3A), and between about 0 and 25 mm from the longitudinally-directed side edges 21, alternatively between about 5 and 20 mm (as demonstrated by T3 on FIG. 3A). These amounts are based on the shortest distance between an outer edge of an individual embossment feature 24 and the closest respective side edge. In one embodiment, the first embossing pattern 27 (combined area of the individual embossment features 24) covers between about 0.5 and 10 percent of the middle region total surface area, alternatively between about 2 and 8 percent (the surface area defined by the middle region transverse direction side edges 23 and the longitudinally-directed side edges 21 (limited portions thereof) which together surround the middle region).

The end regions 25, 26 have relatively shorter maximum heights H3, which each are less than that maximum height H1 of the middle region 22. The end regions may each have the same end region maximum height or may be of different heights. The end regions 25, 26 each include at least a relatively shallow second embossing pattern 29 (made up of individual embossment features 29A). Such embossment features 29A may be recesses (not shown) or instead appear as protrusions 29A which extend outward from the absorbent core layer wearer-facing surface 18A and that are surrounded by trough-like features. In one embodiment, the second embossing pattern 29 may include both protrusions (positive embossments) and recesses (negative embossments). For example, as shown, the overall embossment pattern 29 of absorbent core layer 18 includes raised protrusions 29A and a surrounding trough-like embossment feature 29B, both of which have a height less than that of the middle region 22.

The end regions may in a further alternative embodiment, also include relatively deeper embossing patterns (a third pattern) between the second embossing pattern embossment features 29A (not shown). The end regions 25, 26 include apertures 31 between, and in some embodiments, surrounding the second embossing pattern 29 embossment features 29A. For example, in FIG. 2B, the apertures 31 are shown within the trough-like embossment feature 29B. In the illustrated embodiments of FIGS. 1A, 2A, the first and second embossing patterns 27, 29 include individual circular embossment features (although it is contemplated that they may be of any geometric shape, such as square, hexagonal, rectangular, oval, or abstract, that they may be of the same shapes between regions, or of different shapes between regions). Circular apertures 31 are also illustrated. In one embodiment, the second embossing pattern 29 may cover between 10 and 100 percent of the total area of each end region, alternatively between about 20 and 70 percent.

The apertures 31 illustrated in the end regions, are also of circular or dot-like shapes when viewed from the wearer-facing surface of the absorbent core layer 18 in FIG. 2A, but may alternatively be of other geometric shapes within the end regions. As illustrated in FIG. 2A, the apertures 31 may be aligned along the absorbent core layer longitudinal direction. Such alignment enhances the end regions' ability to bend with a wearer's movements. Alternatively, they may be aligned along the transverse direction (not shown).

As noted, the first embossing pattern 27 is made up of a pattern of individual embossment features 24 which are relatively deep compared with other embossments within the absorbent article 10 and absorbent core layer 18. Such first embossing pattern 27 for example, includes individual embossment features 24 each having a height H4 (or depth of the embossment feature). Essentially, the depth H4 of the individual embossment features 24 of the first embossing pattern 27 are, in one embodiment, between about 0.2 and 6 mm, alternatively between about 0.8 and 3 mm (measured from upper edge to lowest point). If the middle region 22 includes apertures 46 (as seen in FIGS. 1G, 1H), such apertures will be of the same height as the height H1 of the middle region 22 (maximum height of the absorbent core layer). In one embodiment, the ratio of H4 to H1 is between about 0.10 to 1 to 0.99 to 1, alternatively, between about 0.30 to 1 to 0.70 to 1. The walls of the individual embossment features 24 are illustrated as being parallel, but may alternatively taper. While the individual embossment features 24 penetrate deeply within the middle region 22 (and desirably the central area), they do not pierce both outer side surfaces of the absorbent core layer middle region. For instance, the individual embossment features 24 are located on the wearer-facing surface 18A of the absorbent core layer 18, but do not penetrate through the layer to exit the garment-facing surface 18B of the absorbent core layer 18.

As illustrated in FIG. 2A, the first embossing pattern 27 in one embodiment, is in the overall shape of a centrally located dog bone, consisting of discrete circular embossment features 24. Areas 33 of the middle region 22 having no embossment features, surround the central dog bone shaped embossed region on all sides of the middle region 22.

The end regions 25, 26 are, in one embodiment, each of the same length L4, L5 such as between about 10 and 150 mm each, alternatively, between about 30 and 100 mm each, alternatively, at least one end region being between about 10 and 60 percent of the total length L2 of the absorbent core layer 18. In an alternative embodiment, the lengths of the end regions L4, L5 are not equal, such as in a feminine hygiene overnight-style pad (not shown). In such an asymmetric-shaped pad having an end region at the back of the absorbent article 10 (which is to be positioned under a wearer's buttocks region), the back end would be longer than the front end of the absorbent article 10. However, even in such an embodiment, the middle elevated region 22 would be positioned beneath the area of a wearer's anatomy from which exudate would be initially excreted.

The end regions illustrated in FIG. 1A, 2A, 2B each utilize the same second embossing pattern 29. It should be understood that such second embossing pattern 29 need not be the same for each of the end regions 25, 26. However, for ease of description and manufacture, they are illustrated with the same design of circular protrusions 29A surrounded by a recessed trough-like embossment feature 29B. In one embodiment, as shown in FIG. 2A, the end region embossing pattern (second embossing pattern 29) extends across the entire area of the end regions 25, 26 (as illustrated), and includes at least two different height planes, defined by H2, H3 in FIG. 2B. The second embossing pattern 29 of the end regions 25, 26 in FIG. 2B, includes a stepped pattern that defines the protruded embossment features 29A. For instance the height of the protrusion H3 is the combination of the lower level height H2 in addition to the protruded height H5. The height of the middle region H1 is larger than the lower level height H2 by an amount H6 (as seen in FIG. 2B).

In the case of the second embossing pattern 29, the stepped pattern may include a series of depressed steps (as illustrated in cross-sectional view) in which the first step height (defined by H5) ranges from between about 0.05 and 1.5 mm, alternatively about 0.2 mm. This is also the height of the trough-like recess embossment feature 29B. In one embodiment, the height H6 is between about 0.1 mm and 8 mm, alternatively between about 0.5 mm and 5 mm. The height H3 (maximum height of end regions) is, in one embodiment, between about 0.55 and 4 mm, alternatively between about 0.7 and 2.5 mm. The overall height of the absorbent article H7 (as shown on FIG. 1B) is in one embodiment, between about 1 and 10 mm, alternatively, between about 1.5 and 5.0 mm.

The apertures 31 which pierce the absorbent core layer only at the end regions 25, 26 between the embossing patterns 29, may in one embodiment also be positioned so as to be present across the entire end regions 25, 26 (as shown). In this fashion, the end regions 25, 26 may demonstrate uniform flexibility (softness) at these regions as a result of the piercing of the material from the wearer-facing surface 18A to the garment-facing surface 18B. Such apertures are in one embodiment, not only aligned along the longitudinal direction of the absorbent core layer, but also are oriented along the longitudinal direction of the absorbent core layer.

The first and second embossing patterns 27, 29 are, in one embodiment, only present upon the wearer-facing surface 18A of the absorbent core layer 18. The first and second embossing patterns 27, 29 on the wearer-facing surface of the absorbent core layer 18A allow for the capture and rapid transmission of body exudate from the surface of the absorbent core layer closest to the initial deposition location. While the apertures 31 illustrated in FIGS. 2A, 2B are shown as circular shapes (from the top plan view), it should be appreciated that they can be present as any geometric or abstract shape, such as for example as diamonds, squares, ovals, or triangular opened channels (when viewed from the top plan view). While the walls of the apertures 31 are illustrated as being tapered in FIG. 2B, it should also be understood that the walls may be parallel with one another.

As seen in FIG. 3A, the second embossing pattern 35 may be formed of different shapes from those of the first embossing pattern 27. For example, in FIG. 3A the second embossing pattern forms a series of diamond-like protrusions, formed from separated raised segments 35 or dashes which surround a trough-like diamond feature 35A.

Furthermore, rather than being mere dot-like in shape, such apertures may instead be in the form of separated, dash-like perforations, or slits 36, positioned at the end regions 25, 26 in addition to the second embossing patterns 35. The slits 36 may be aligned along primarily one direction of the absorbent core layer 18, and be positioned regularly between the embossment pattern features 35. Such slits may be produced using traditional slitting or cutting techniques as are known in the art, and like previously described apertures 31, extend across a large percentage of the total area of the end regions. Such slits may be oriented along primarily the absorbent core layer longitudinal direction (as seen in FIG. 3A, 3B), alternatively along the absorbent core layer transverse direction (not shown), or along a combination of the absorbent core layer longitudinal and transverse directions (not shown), such that the slits or the paths of the separated slits crisscross across the end regions. By orienting the apertures or slits along two directions, the flexibility of the end regions can be further increased along multiple directions.

Rather than including just elongated slits, the end regions may alternatively include a combination of dot-like apertures and slits (not shown). Furthermore, the number of apertures or slits may be increased per unit area so as to increase the softness/flexibility of the end regions. For example, higher densities of dot-like or slit apertures at the end regions 25, 26 may provide desired increased flexibility. In the case of slits, the slits may be placed in a configuration such that they cross one another either in a diagonal fashion or in a configuration along both the longitudinal and transverse directions. By including either apertures or slits in an orientation primarily along the absorbent core layer longitudinal direction (separated by a distance L9), the flexibility of the end regions 25, 26 can be substantially enhanced even though there are continuous embossing patterns across such end regions.

In this way, an absorbent core layer can be produced that demonstrates both reduced bulk at least at the end regions, and flexibility at the same embossed regions that would ordinarily be stiff, but for the presence of the apertures. In one embodiment, apertures are present in the end regions in an amount of between about 1 and 10 per cm$^2$, alternatively between about 2 and 6 per cm$^2$. Alternatively, the apertures have a distance between one another (between closest adjacent, aperture outer edges L9) of between about 1 and 30 mm, alternatively between about 2.5 and 10 mm. In one embodiment, the individual embossment features 24 (or apertures as explained in connection with FIGS. 1G and 1H) of the middle region have a distance between the features L7 (between adjacent embossment or aperture feature closest outer edges) of between about 1 and 30 mm, alternatively between about 2 and 15 mm. Alternatively, the individual embossment features 29A of the end regions have a distance L6 between them (individual embossment feature outer edges, such as the outer edge of the circles of 29A) of between about 1 and 20 mm, alternatively of between about 2 and 10 mm. It should also be appreciated that the distances between adjacent embossment features or apertures may be regular or irregular.

As seen in FIG. 1C, a longitudinal cross-sectional view of an alternative embodiment of the absorbent article including the absorbent core layer 18 of the invention is shown. As seen in the figure, the absorbent article 10 includes additional layers. In particular, either a fluid surge, distribution or transfer layer 41 (as are known in the absorbent article art) is illustrated between the absorbent core layer 18 and the topsheet layer 16. Either a distribution layer or another absorbent core layer 42 is also illustrated between the backsheet layer 17 and the absorbent core layer 18. It should be appreciated that while not shown, additional functional layers or absorbent core layers are also considered to be within the scope of the disclosure. Further, the absorbent core layer 18 that is embossed and apertured as described herein, may itself be formed from one or multiple layers.

As seen in FIG. 1D, a longitudinal direction, cross-sectional view of an alternative embodiment of the absorbent article, including the absorbent core layer 18 of the invention is shown. As seen in the figure, the absorbent article 10 includes additional layers. In particular, an apertured fluid transfer layer 41A is illustrated between the absorbent core layer 18 and the topsheet layer 16. The apertured fluid transfer layer 41A defines a relatively large annular opening 41B (such as in the shape of an oval extending along the layer longitudinal direction) in its center, which annular opening 41B is positioned directly above the first embossing pattern 27 of the middle region 22. Such an annular opening 41B directs exudate to the absorbent core layer, and also creates a well-like structure for retaining excess exudate until it can be absorbed fully into the absorbent core layer.

As seen in FIG. 1E, a longitudinal, cross-sectional view of a further alternative embodiment of the absorbent article including the absorbent core layer 18 of the invention is shown. As seen in the figure, the absorbent core layer 18 itself defines an overall recess or concavity as a result of the overall first embossing pattern 27 (aside from individual recesses defined by the individual embossment features 24) in its middle region 22, along the wearer-facing surface 18A. The recess or concavity extends along the layer longitudinal direction. The recess or concavity is formed by the close proximity and progressively lower heights of the individual embossment features 24 (lower heights approaching the center of the absorbent core layer middle region from both ends). Such recess or concavity assists in capturing body exudates that are passed through the topsheet layer 16 and retains such exudate while it is being further absorbed into the core layer. Since the sides of the middle region are of higher elevation than the central area, the exudate stays within the well-like feature rather than running off of the side edges.

As seen in FIG. 1F, a longitudinal cross-sectional view of a further alternative embodiment of the absorbent article including the absorbent core layer 18 of the invention is shown. As seen in the figure, the absorbent core layer 18 defines another overall recess or concavity (aside from individual recesses defined by the individual embossment features 24) in its middle region 22 central area, along the wearer-facing surface 18A. The recess or concavity is formed by the close proximity and similar lower/rounded top surfaces of the walls 45A of the individual embossment features 24. Such recess or concavity assists in capturing body exudates that are passed through the topsheet layer 16 and maintaining them in a well-like structure until they can be fully absorbed into the absorbent core layer 18.

As seen in FIG. 1G, a longitudinal cross-sectional view of a further alternative embodiment of the absorbent article including the absorbent core layer 18 of the invention is shown. As seen in the figure, the absorbent core layer 18 includes in its middle region 22 a combination of embossment features 24 and apertures 46. Such apertures are located between negative embossment features (depressions). Such apertures further direct body exudate through channels to lower levels of the absorbent core layer.

As seen in FIG. 1H, a longitudinal cross-sectional view of a further alternative embodiment of the absorbent article including the absorbent core layer 18 of the invention is shown. As seen in the figure, the absorbent core layer 18 includes in its middle region 22 only apertures 46, and no embossment features. Such apertures direct body exudate through channels to lower levels of the absorbent core layer and assist in the rapid intake of the exudate.

As seen in FIG. 4, a top plan view of still another alternative embodiment of the absorbent core layer 18 is illustrated. In the absorbent core layer 18, the individual embossment features 24 of the middle region 22 are arranged in an alternative embossing pattern 28, that is in an overall shape of an oval. As with previously described middle region embossing patterns, elevated side areas 33, 33A, 33B surround the central area in the middle region, and the embossing pattern 28 is positioned symmetrically about the central longitudinal direction of the absorbent core layer 18.

As seen in FIG. 5, a top plan view of still a further alternative embodiment of the absorbent core layer 18 is illustrated. As seen in the figure, the end regions 25 and 26 include a second embossing pattern 36 that is in a shape resembling a series of adjacent, noncircular sectors. As with the pattern of FIG. 2A, the embossing pattern of FIG. 5 includes pillow-like, protruding centers 36A, which extend out of the absorbent core layer surface on the wearer-facing surface of the absorbent core layer, and towards the wearer-facing surface of the absorbent article. The protruding centers are surrounded by a trough-like recess 36B. Apertures in the form of curved slits 37 are positioned within the trough-like embossments 36B. Such curved slits extend along both the transverse and longitudinal directions of the absorbent core layer 18. They are generally aligned with one another as well.

Finally, as seen in FIG. 6, a top plan view of a further alternative design of an absorbent core layer 18 is illustrated. In the alternative embodiment, rather than having the middle region 22 include entirely parallel or generally parallel transverse direction side edges 23, the middle region includes extended edges with portions that are parallel and portions that are not 23A. These extended edges form the end regions into a "V"-like shape 38. In this fashion the middle region includes transverse side edges 23 which are partially parallel, and other edges 23A which partially surround the end regions 25, 26.

The liquid permeable topsheet layer 16 may be manufactured from any number of conventional materials commonly used as a wearer-facing surface on an absorbent article. For example, non-limiting examples of such topsheet layer materials include fibrous nonwoven sheet materials, such as spunbond, spunlace, meltblown, and carded web materials (such as thermally bonded carded webs (TBCW), through-air bonded carded webs (TABCW)), fibrous woven sheet materials, apertured polyolefinic film or apertured fibrous nonwoven materials (single and dual apertured), and laminate combinations of the foregoing materials. Further, monolayered or multilayered sheet materials of the foregoing can also be used as the liquid permeable topsheet layer 16. Particularly, carded web materials may be made from staple, bicomponent fibers as are known in the art. Materials that may be used in the topsheet layer 16 include synthetic fibers, such as polyolefinic materials. Such topsheet layers 16 may themselves be embossed. Suitable topsheet layer materials include, but are not limited to those described in U.S. Pat. No. 4,397,644 to Matthews et al., U.S. Pat. No. 4,629,643 to Curro et al., U.S. Pat. No. 5,188,625 Van Iten et al., U.S. Pat. No. 5,382,400 to Pike et al., U.S. Pat. No. 5,533,991 to Kirby et al., U.S. Pat. No. 6,410,823 to Daley et al., and United States Publication 2012/0289917 to Abuto et al., each of which is hereby incorporated by reference thereto in its entirety, to the extent that they are not inconsistent with this disclosure.

The topsheet layer 16 may be a two layer (such as in the same or two different horizontal planes) or multi-component material with a central, longitudinally directed section positioned along and straddling the central longitudinal direction of the article, with lateral side-topsheet sections flanking and joined to each side (or side longitudinal edge) of the central longitudinally directed topsheet layer section. The central topsheet section may be made for example, from the aforementioned TABCW materials or it may be made from a perforated film that has been treated to be hydrophilic. The lateral side topsheet sections may be made from a different fibrous nonwoven material which is joined to the central longitudinally directed section, such as by adhesive or thermal bonding. Such a two layer topsheet configuration is described for example, in U.S. Pat. No. 5,961,505 to Coe, U.S. Pat. No. 5,415,640 to Kirby and U.S. Pat. No. 6,117,523 to Sugahara, each of which is hereby incorporated by reference thereto in its entirety, to the extent that they are not inconsistent with this disclosure. It is also contemplated that such two layer topsheet materials may additionally include longitudinally extending elastic strand components (not shown) along their side edges to lift up components of the side-topsheet materials during use, thereby forming physical barriers or cupping features on the article so as to allow a fit more closely aligned to the body of a wearer. The topsheet layer 16 may also be treated so as to impart other properties to the wearer-facing surface. Examples of additional treatments include application of skin health agents, coloring agents, odor control agents, stain masking agents and the like.

The basis weight of nonwoven webs to be used as liquid permeable topsheet layers 16 may generally vary, such as from about 5 grams per square meter ("gsm") to 150 gsm, in some embodiments from about 10 gsm to about 125 gsm, and in some embodiments, from about 15 gsm to about 120 gsm. In one embodiment, the topsheet layer 16 is a through-air bonded carded web (thermally bonded) having a basis weight of about 25 gsm.

As noted, optionally, a fluid transfer or surge layer may be attached to the garment-facing surface 16B of the liquid permeable topsheet layer 16. Such additional fluid transfer layers include, but are not limited to, bonded carded webs, hydroentangled nonwoven webs, or spunbond webs.

The absorbent core layer 18 can itself comprise a single layer or multiple layers and these one or more layers can themselves comprise similar or different materials, although a single layer of homogenous composition material is desirable in one embodiment. Highly absorbent core layers often include, but are not limited to, hydrophilic batts or webs containing wood pulp fibers, superabsorbent particles or fibers (known as SAP or SAM), synthetic wood pulp fibers, synthetic fibers, airlaid material, coform materials, hydrophilic foam materials, and combinations thereof. The absorbent core layer 18 may comprise any one of a number of materials and structures, the particular selection of which will vary with the desired loading capacity, flexibility, body fluid to be absorbed and other factors known to those skilled in the art. By way of example, suitable materials and/or structures for the absorbent core layers include, but are not limited to, those described in U.S. Pat. No. 4,610,678 to Weisman et al., U.S. Pat. No. 6,060,636 to Yahiaoui et al., U.S. Pat. No. 6,610,903 to Latimer et al., U.S. Pat. No. 7,358,282 to Krueger et al., and United States Patent Publication 2010/0174260 to Di Luccio et al., each of which is hereby incorporated by reference thereto in its entirety, to the extent that they are not inconsistent with this disclosure. The absorbent core layer 18 may be wrapped in a variety of materials, such as tissue, nonwoven sheeting, apertured film layers, or mesh/netting.

The shape of the absorbent core layer 18 (while generally shown as an oblong configuration to generally mimic the outer peripheral shape of the absorbent article 10 can vary as desired and can comprise any one of various shapes including, but not limited to, generally triangular, rectangular, dog-bone and elliptical shapes. In one embodiment, the absorbent core layer 18 has a shape that generally corresponds with the overall peripheral shape of the absorbent article 10 such that the absorbent core layer 18 terminates proximate the peripheral seal region 40. The dimensions of the absorbent core layer 18 can be substantially similar to those of the absorbent article 10, however it will be appreciated that the dimensions of the absorbent core layer 18 while similar, will often be slightly less than those of the overall absorbent article 10 in order to be adequately contained therein, and desirably sealed around the edges.

In one embodiment, the absorbent core layer 18 is a homogeneous fluff core layer, having a basis weight range of between about 60 and 350 gsm in which a fluff layer is wrapped with a tissue sheet. In such a core structure, the fluff component would have a basis weight range of between about 50 and 340 gsm, with the basis weight of the tissue wrap being between about 12 and 25 gsm. In an alternative embodiment, the homogeneous absorbent core layer would be a mixture of fluff and SAP surrounded by a tissue wrapper. In such a structure, the basis weight of the layer would be between about 60 and 350 gsm, the basis weight of the fluff component would be between about 50 and 340 gsm, the basis weight of the SAP component would be between about 0.1 and 100 gsm, and the basis weight of the tissue wrapper would be between about 12 and 25 gsm. In such embodiments, traditional cellulosic fluff and SAP would be used, and the layer would be constructed using traditional manufacturing techniques as are known in the art. Such techniques include airlaid techniques. The tissue wrap is in one embodiment placed about either all sides of the core layer, the top and bottom surfaces of the core layer, or is only used as a carrier sheet for supporting the fluff and SAP mixture of materials. In an alternative embodiment, the absorbent core layer 18 can be a multiple layer core such as of an airlaid layer bonded to a fluff core layer.

As noted, the individual layers comprising the absorbent article can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis.

The liquid impermeable backsheet layer 17 functions to isolate absorbed fluids from the wearer's garments or bedding, and therefore can comprise a variety of liquid-impervious materials. In one aspect, the liquid impermeable backsheet layer 17 may optionally comprise a material that prevents the passage of liquids but allows air and water-vapor to pass there-through. The liquid impermeable backsheet layer 17 can comprise a single layer or multiple layers, and these one or more layers can themselves comprise similar or different materials. Suitable liquid impermeable backsheet layer 17 materials include, but are not limited to, polyolefin films, nonwovens, nonwoven laminates, and film/nonwoven laminates. The particular structure and composition of the liquid impermeable backsheet layer may be selected from various known films and/or fabrics with the particular material being selected as appropriate to provide the desired level of liquid barrier, strength, abrasion resistance, tactile properties, aesthetics (such as texture and printability) and so forth. Suitable backsheet layer materials include, but are not limited to, those described in U.S. Pat. No. 4,376,799 to Tusim et al., U.S. Pat. No. 4,578,069 to Whitehead et al., U.S. Pat. No. 5,695,849 to Shawver et al, U.S. Pat. No. 6,075,179 et al. to McCormack et al., and U.S. Pat. No. 6,376,095 to Cheung et al., each of which is hereby incorporated by reference thereto in its entirety, to the extent that they are not inconsistent with this disclosure. The liquid impermeable backsheet layer 17 may be breathable or nonbreathable, as may be desired. In one embodiment, the liquid impermeable backsheet layer 17 is a breathable poly-olefinic film having a basis weight of between about 18 and 40 gsm, alternatively between about 20 and 30 gsm, such as of a polyethylene film.

As noted, the absorbent articles 10 of the invention may include other additional features as are generally known in the art. Such features may include wing or tab-like features 15, which are desirably extensions of the liquid permeable second topsheet layer and liquid impermeable backsheet layer that extend out from the opposing lateral side edges of the article. Such wings may also be nonintegral in construction, either being attached only to the topsheet layer 16 or the backsheet layer 17. The articles may further be individually wrapped in a pouch, such as those which are commonly known in the art. In such an instance, such article may be releasably fastened to the inside surface of such pouch for ease of article handling and eventual disposal. Finally, the absorbent article 10 of the invention may include visual cues, such as coloration, in order to highlight the presence of the absorbent core layer 18 or the three distinct regions of the absorbent core layer 18. Such visual cues can assist in communicating the functionality of the absorbent core layer 18, and the placement of the absorbent article such that the middle region 22 of the absorbent core layer 18 is positioned in an appropriate location under the wearer's anatomy.

With the absorbent core layer 18 as described, an absorbent layer is disclosed which provides the benefits of diverse embossing patterns at different absorbent core layer regions, without sacrificing comfort. Apertures are used in one embodiment, only at the layer's longitudinal end regions in order to provide flexibility in the thinner end regions (that would normally be stiffer as a result of embossment compression), which flexibility allows the wearer to move within their undergarments with less discomfort. Such apertures will also allow for greater breathability of the absorbent article over the useful life of the article, since such liquid impermeable backsheet layers and liquid permeable topsheet layers are frequently both breathable. Further, by use of a compressed absorbent core layer, articles employing such layer may be constructed to be thinner at the ends, thereby enhancing the inconspicuous nature of the pad profile when viewed through a wearer's undergarments and outer garments, and also so as to more easily allow for the folding of the articles prior to use, since fold lines of the articles can be positioned to correspond to the borders of the middle region and end regions.

It has been found that when a pattern of relatively deep individual embossment features are oriented on the wearer-facing surface, central area of an absorbent core layer, such as in an overall dog bone, oval, or elongated rectangular shaped configuration, a centralized fluid-capture, well-like feature is created. If the individual embossment features are deep enough, large enough, and in close enough proximity to one another, the resulting well-like structure allows for a relatively large amount of body exudate to be temporarily captured within this well-like structure, thereby avoiding leakage of exudate off of an article's longitudinally directed side edges. If such overall embossing pattern is of a dog bone shape, or otherwise concave towards the central longitudinal direction of the absorbent core layer, soft and cushion-like longitudinal side edges are created on the absorbent core layer. The embossing pattern also creates a stabilized, and stiffened central portion (in the shape of the overall pattern 27) within the layer middle region, which stabilized and stiffened central portion is adjacent the backsheet layer (at least on one embodiment). Such feature assists in maintaining the core layer integrity in this region.

Furthermore, it has been found that by aligning the spaced-apart apertures along the longitudinal direction of the absorbent core layer at the end regions, additional flexibility is provided to the core layer, and ultimately to the absorbent article (at the article ends). By increasing the number of spaced-apart and aligned apertures in the end regions (along the absorbent core layer longitudinal direction), flexibility can be further increased. In one embodiment, such linear patterns of spaced-apart apertures are parallel to/with the central longitudinal direction of the absorbent core layer (and absorbent article). A greater number of sets of linear, spaced-apart apertures results in greater core layer and article flexibility at the end regions.

In one embodiment, the absorbent core layer is manufactured from a sheet material that initially has a uniform basis weight, density, and height. Such absorbent core layer is in one embodiment air-formed. Such embossed and apertured absorbent core layer may be manufactured using a single set of rolls or multiple pairs of mated rolls, such as for example, a first pair designed to emboss and/or aperture the middle region and second pair designed to emboss and aperture the end regions. A single embossing roll set or a second embossing roll set may also include enlarged pins so as to also provide the aperturing of the middle and/or end regions.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent core layer for absorbing and retaining body exudate, said absorbent core layer including a longitudinal, transverse, and depth direction and comprising: a first end region, a second opposing end region, and a middle region positioned between said first and second opposing end region, said middle region for placement under the source of body exudate;
    said middle region including a first embossing pattern having individual embossment features, said middle region having a first maximum thickness,
    said first end region and said second opposing end region each including a second embossing pattern having individual embossment features, different from said first embossing pattern, and having apertures between said second embossing pattern individual embossment features, said first end region and said second opposing end region each having a second maximum thickness, wherein said second maximum thickness is less than said first maximum thickness.

2. The absorbent core layer of claim 1, wherein said middle region includes a central area said middle region including a first embossing pattern, said first embossing pattern in said middle region being present in said central area.

3. The absorbent core layer of claim 2, wherein said first embossing pattern is comprised of individual embossment features each in the shape of a circle.

4. The absorbent core layer of claim 1, wherein said absorbent core layer is of a single layer construction.

5. The absorbent core layer of claim 1, wherein said regions are distinguished from one another along parallel lines.

6. An absorbent article having a topsheet layer, a backsheet layer and an absorbent core layer sandwiched and sealed between said topsheet and backsheet layers, said absorbent core layer comprising the absorbent core layer of claim 1.

7. The absorbent core layer of claim 1, wherein said end regions extend outward from said middle region along the longitudinal direction.

8. The absorbent core layer of claim 1, wherein said middle region further includes apertures.

9. An absorbent core layer for absorbing body exudate, said absorbent core layer having a longitudinal, transverse, and depth direction and comprising a first longitudinal end region, a second opposing longitudinal end region, and a middle region positioned between said first longitudinal end region and said second opposing longitudinal end region, said middle region for placement under the source of body exudate;
    said middle region including a first embossing pattern of individual embossment features, and having a first thickness, said first longitudinal end region and said second opposing longitudinal end region including a second embossing pattern of individual embossment features different from said first embossing pattern embossment features, and having apertures between said second embossing pattern individual embossment features, said first and second opposing longitudinal end regions having a thickness less than that of said middle region, and wherein said apertures are selected from the group consisting of dot-like apertures and slits.

10. The absorbent core layer of claim 9, wherein said first and second opposing longitudinal end regions have a thickness of between about 0.75 mm and 5.0 mm.

11. The absorbent core layer of claim 9, wherein said embossing pattern of said first and second opposing longitudinal end regions are configured in the shapes of either circles, squares, ovals, diamonds, lines, dots, sectors, or waves, and said apertures are in the shapes of either circles or lines.

12. The absorbent core layer of claim 9, wherein said second embossing pattern of said first and second opposing longitudinal end regions covers between about 10 and 100 percent of the surface area of each end region.

13. The absorbent core layer of claim 9, wherein said apertures are aligned along either the longitudinal or transverse direction.

14. The absorbent core layer of claim 9, wherein said apertures are oriented along the longitudinal direction.

15. The absorbent core layer of claim 9, wherein said apertures are present at each of the end regions so as to cover between about 2 and 20 percent of each end region total surface area.

16. The absorbent core layer of claim 9, wherein said first embossing pattern of said middle region covers between about 0.5 and 10 percent of the middle region surface area.

17. The absorbent core layer of claim 9, wherein the absorbent core layer has an overall length of between about 135 mm and 400 mm and the middle region has a length of between 20 and 80 percent of the overall length.

18. The absorbent core layer of claim 17, wherein one of the end regions may be between about 10 and 60 percent of the overall length.

* * * * *